United States Patent [19]

Lindemann et al.

[11] 4,382,036
[45] May 3, 1983

[54] PYROPHOSPHOBETAINES

[75] Inventors: Martin K. O. Lindemann, Bridgewater; Elvin R. Lukenbach, Somerset; Robert J. Verdicchio, Succasunna, all of N.J.

[73] Assignee: Johnson & Johnson Baby Products Company, New Brunswick, N.J.

[21] Appl. No.: 263,959

[22] Filed: May 15, 1981

[51] Int. Cl.$^3$ ............................................. C07F 9/08
[52] U.S. Cl. .................................. 260/403; 260/924; 260/933; 544/57; 544/151; 544/337; 548/112
[58] Field of Search ................ 260/933, 403; 544/157

[56] References Cited

U.S. PATENT DOCUMENTS 3,304,349  2/1967  Shen ..................................... 260/933
4,283,542  8/1981  O'Lenick, Jr. et al. ............. 260/945

Primary Examiner—Anton H. Sutto
Attorney, Agent, or Firm—Steven P. Berman

[57] ABSTRACT

Novel amphoteric and zwitterionic betaine compounds containing at least one anion having a phosphorus-oxygen-phosphorus bond and processes for their preparation are described.

4 Claims, No Drawings

PYROPHOSPHOBETAINES

BACKGROUND OF THE INVENTION

The present invention relates to novel compositions of matter consisting of specific betaine derivatives referred to hereinafter as "pyrophosphobetaines." More particularly, this invention relates to novel amphoteric and zwitterionic betaine compounds containing at least one anion having a phosphorus-oxygen-phosphorus bond.

Betaines and certain substituted betaines including betaines having phosphorus-containing anions in the molecules are known in the art, see for example U.S. Pat. Nos. 4,181,634; 4,215,064; 4,233,192; 4,209,449 and 4,261,911. The pyrophosphobetaines of the present invention exhibit outstanding foaming, cleansing and detergency properties as well as being extremely well-tolerated by human tissue, i.e. they exhibit exceptionally low ocular irritation and oral toxicity and are therefore useful as surfactants in personal care compositions.

SUMMARY OF THE INVENTION

This invention encompasses betaine surfactant compounds of the formula

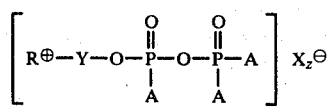  (I)

wherein R, Y, A, X and z are as defined below.

DETAILED DESCRIPTION OF THE INVENTION

The novel pyrophosphate compounds of this invention may be represented by the following general formula

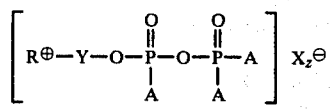  (I)

wherein A is selected from $-O^-$, $-OM$ and $-O-Y-R^+$ with the proviso that at least one A is $-O^-$;

$X^-$ is an anion;

z is an integer from 0 to 3, a value necessary for charge balance;

R is an amine or amidoamine moiety of the formula

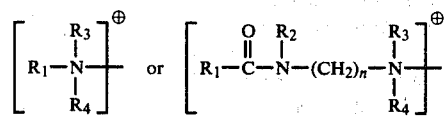

wherein $R^1$ is alkyl, alkenyl, alkoxy, or hydroxyalkyl of from 5 to 22 carbon atoms, each, or aryl or alkaryl of up to 20 carbon atoms, $R^2$ is hydrogen or alkyl, hydroxyalkyl or alkenyl of up to 6 carbon atoms each or cycloalkyl of up to 6 carbon atoms, preferably of from 2 to 5 carbon atoms, or polyoxyalkalene of up to 10 carbon atoms, $R^3$ and $R^4$, which may be the same or different, are selected from alkyl, hydroxyalkyl, carboxyalkyl of up to 6 carbon atoms in each alkyl moiety, and polyoxyalkylene of up to 10 carbon atoms; in addition, $R^3$ and $R^4$ taken together with the nitrogen to which they are attached, may represent an N-heterocycle, e.g., a morpholino structure, in which the Y radical is bonded to a ring atom of said N-heterocycle other than the nitrogen of the R moiety;

n is an integer from 2 to 12;

Y may be alkylene, optionally interrupted by up to 3 oxygen atoms, of up to 12 carbon atoms, which alkylene chain may optionally be substituted with lower alkyl, alkoxy, hydroxy or hydroxyalkyl, e.g., of not more than 10 carbon atoms each;

M is hydrogen, an organic radical selected from alkyl or hydroxyalkyl of up to 6 carbon atoms, polyhydroxyalkyl of up to 10 carbon atoms, glyceryl, cycloalkyl of up to 6 carbon atoms, aryl or arylalkyl of up to 10 carbon atoms, or a salt radical selected from alkali metals (e.g., sodium, potassium or ammonium and substituted ammonium radicals) and alkaline earth metals (e.g., magnesium or calcium).

The term "polyoxyalkalene" as used above in the definition of $R^2$, $R^3$ and $R^4$ may be of the formula $(R^5-O-R^{5'})_m$, wherein $R^5$ and $R^{5'}$ are alkyl of from 1 to 4 carbon atoms and m is an integer from about 2 to 10.

Preferred subgroups of the compounds of formula I can be represented as follows

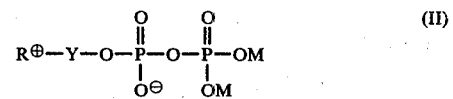  (II)

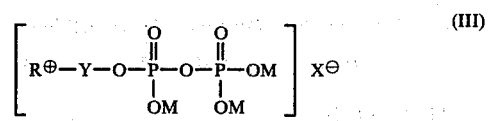  (III)

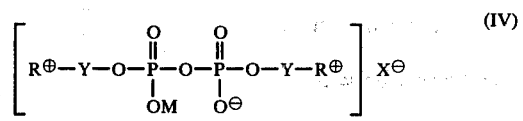  (IV)

The compounds of formula IV are bispyrophosphobetaines containing two quaternary ammonium moieties. Compounds III and IV require the presence of an anion ($X^-$) for charge balance such as halide, phosphate, sulfate, and the like.

The synthesis of these compounds can be carried out according to the following scheme.

The amidoamine R moiety can be prepared by condensing a suitable acid such as lauric, myristic, coconut fatty acids and the like with an aminoalkyl-substituted tertiary amine as follows:

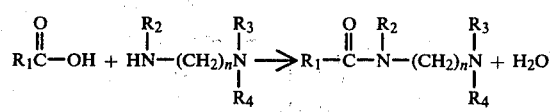

Alternatively, an acid can be reacted with an aminoalkyl-substituted secondary amine followed by further alkylation, i.e. treatment with alkylene oxide.

The pyrophosphate ester is prepared by reacting with $$CH_2\underset{\diagdown O \diagup}{\text{———}}CH-CH_2X$$

$$HO-\underset{OM}{\overset{O}{\overset{\|}{P}}}-O-\underset{OH}{\overset{O}{\overset{\|}{P}}}-OM$$

to yield the corresponding ester $$X-CH_2-\underset{OH}{CH}-CH_2-O-\underset{OM}{\overset{O}{\overset{\|}{P}}}-O-\underset{OH}{\overset{O}{\overset{\|}{P}}}-OM$$

or by reacting $$2CH_2\underset{\diagdown O \diagup}{\text{———}}CH-CH_2X$$

with $$HO-\underset{OM}{\overset{O}{\overset{\|}{P}}}-O-\underset{OH}{\overset{O}{\overset{\|}{P}}}-OM$$

to yield $$X-CH_2-\underset{OH}{CH}-CH_2-O-\underset{OM}{\overset{O}{\overset{\|}{P}}}-O-\underset{OM}{\overset{O}{\overset{\|}{P}}}-O-CH_2-\underset{OH}{CH}-CH_2X$$

Alternatively, $$2X-(CH_2)_n-OH$$

can be reacted with $$P_2O_5$$

to yield the corresponding ester $$X-(CH_2)_n-O-\underset{OH}{\overset{O}{\overset{\|}{P}}}-O-\underset{OH}{\overset{O}{\overset{\|}{P}}}-O-(CH_2)_n-X$$

The pyrophosphobetaine compounds (I) of the invention can be prepared from the corresponding pyrophosphate ester and amine reactants as follows $$R + X-CH_2-\underset{OH}{CH}-CH_2-O-\underset{OM}{\overset{O}{\overset{\|}{P}}}-O-\underset{OM}{\overset{O}{\overset{\|}{P}}}-OM$$
$$\downarrow$$
$$\left[R^{\oplus}-CH_2-\underset{OH}{CH}-CH_2-O-\underset{OM}{\overset{O}{\overset{\|}{P}}}-O-\underset{OM}{\overset{O}{\overset{\|}{P}}}-OM\right] X^{\ominus}$$

-continued- $$2R + X-(CH_2)_n-O-\underset{OM}{\overset{O}{\overset{\|}{P}}}-O-\underset{OM}{\overset{O}{\overset{\|}{P}}}-O-(CH_2)_n-X$$
$$\downarrow$$
$$\left[R^{\oplus}-(CH_2)_n-O-\underset{OM}{\overset{O}{\overset{\|}{P}}}-O-\underset{OM}{\overset{O}{\overset{\|}{P}}}-O-(CH_2)_n-R^{\oplus}\right] 2X^{\ominus}$$

wherein R is an amine reactant of the formula $$R_1-\underset{R_4}{\overset{R_3}{\overset{|}{N}}} \quad or \quad R_1-\overset{O}{\overset{\|}{C}}-\underset{R_4}{\overset{R_2}{\overset{|}{N}}}-(CH_2)_n\underset{}{\overset{R_3}{\overset{|}{N}}} \quad or \quad (CH_2)_o\underset{Z}{\diagup}\overset{R_6}{\overset{|}{N}}\diagdown(CH_2)_p$$

in which the radicals are as defined above; o and p are integers of from 1 to 4 and Z is O, NH or S.

The reactions to form the pyrophosphobetaine compounds of the present invention are generally carried out in aqueous systems at temperatures of from about 50°–100° C. The resulting pyrophosphobetaine compounds have a pH in solution of from about 6 to 8 depending on the specific structure, i.e. the nature of the hydrophobe and the degree of mono-or di-substitution.

These novel pyrophosphobetaines are good surfactants and quite unexpectedly exhibit good foam volume as well as outstanding foam stability in comparison to commercially available amphoteric and zwitterionic surfactants. This was determined by an adaption of the well known Ross-Miles foam test [Oil and Soap 18, 99 (1941)] in the following manner:

Lanolin, anhydrous, cosmetic grade is mixed with dioxane (technical grade) in the proportion of 2.5 grams lanolin and 100 grams of dioxane. The lanolin is first mixed with 25 cc. of dioxane. This mixture is heated over a steam bath to 45° C. in order to dissolve the lanolin in the dioxane. The remainder of the dioxane is then added and mixed. This lanolin-dioxane solution, which is stored in an amber bottle, should be prepared fresh on the day that the tests are run.

The composition to be tested is diluted by adding 376 cc of distilled water to 4 grams of the composition and then by adding 20 cc of the lanolin-dioxane solution described above while mixing. Heat is produced when the lanolin-dioxane solution is added to the solution of the composition in water and care must be taken in adjusting the temperature of this solution to 24°–25° C. Both of these intermediate solutions should therefore be adjusted to 23° C. before mixing. The cooling of the lanolin-dioxane solution should be gradual in order to avoid precipitation of the lanolin. This will produce a final solution with a temperature of 24°–25° C.

The final solution of the composition to be tested, water, dioxane and lanolin described above, is then run in a modified Ross-Miles foam column in the usual way. All tests are conducted in duplicate, and the average of the two results is taken. Foam stability is determined by measuring the decay in foam height after two minutes, expressed as a percentage of the original height.

Typical foam values obtained utilizing the above procedure for alkylamidopyrophosphobetaines, an alkylamido betaine and an alkylamido sultaine are as follows:

| Surfactant | Example No. | Foam Volume (ml) | % Decay (after 2 min) |
|---|---|---|---|
| Lauric amido 3-hydroxypropyl-pyrophosphobetaine | VII | 241 | 20 |
| Myristic amido 3-hydroxypropyl-pyrophosphobetaine | VIII | 215 | 25 |
| Cocamido Propylbetaine | — | 225 | 31 |
| Cocamido Propylsultaine | — | 200 | 60 |

As can be seen from the above results, the pyrophosphobetaines of the present invention exhibit excellent foam volume and when compared to the betaines and sultaines provide significantly better foam stability.

In addition, the pyrophosphobetaine compounds of the present invention possess a surprisingly low ocular irritation potential when compared to commercially available amphoteric and zwitterionic surfactants. The test employed is the modified Draize Test (J. H. Draize et al., Toilet Goods Assn. No. 17, May 1952, No. 1, Proc. Sci. Sect.).

In this testing method, a 0.1 ml sample of neutral solution of the compound under investigation is dropped into one eye of an albino rabbit, the other eye serving as a control. Six rabbits are employed for each compound.

Observations are made after 1, 24, 48, 72 and 96 hours and 7 days after initial instillation; second and third instillations are made after the 24 and 48 hour readings. Results may vary from substantially no change or only a slight irritation in the appearance of the rabbit's eye after 7 days to severe irritation and/or complete corneal opacity. Ocular lesions are scored for the cornea, iris and conjunctiva with a higher number indicating greater ocular irritation and the scores are added to give a total numerical value for each reading for 6 rabbits and averaged. The averaged score is an indication of the irritation potential of the composition under test. Based on the averaged score, descriptive irritation evaluation may be given, e.g. none, slight, moderate, severe, etc.

Typical results obtained utilizing the above procedure for alkylamidopyrophosphobetaines, an alkylamido betaine and an alkylamido sultaine are as follows:

| Compound | Eye Irritation Potential | | | | | |
|---|---|---|---|---|---|---|
| | 1 hr | 24 hrs | 48 hrs | 72 hrs | 95 hrs | Day 7 | Rating |
| Lauric Amido-3-hydroxypropyl pyrophospho-betaine | 8.5 | 3.0 | 5.0 | 4.3 | 3.7 | 0.3 | Slight |
| Myristic Amido-3-hydroxypropyl pyrophospho-betaine | 12.3 | 2.7 | 6.0 | 6.2 | 4.3 | 2.0 | Slight to Moderate |
| Cocaimido-3-hydroxypropyl sulfobetaine | 11.7 | 4.2 | 9.3 | 13.2 | 11.2 | 5.8 | Severe |
| Cocamido-propylbetaine | 15.3 | 8.5 | 15.5 | 25 | 24.3 | 4.3 | Severe |

(all tests were conducted at 3% wt/wt)

As can readily be seen from the above results, the compounds of the present invention exhibit significantly less eye irritation potential than the betaines and sulfobetaines.

The following examples illustrate the preparation of the compounds of the present invention but are not intended to be limiting thereof. Precursors set forth in the examples include, inter alia, the following, wherein the letter designation corresponds to that used in the experimental procedure.

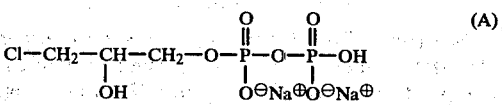

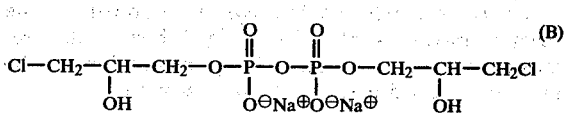

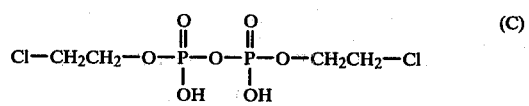

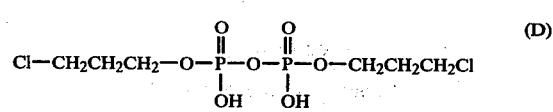

EXAMPLE I

Preparation Of Reactant A 1000 parts of deionized water are charged into a reactor equipped with external heating and overhead stirring facilities. 446 parts of $Na_4P_2O_7 \cdot 10\ H_2O$ and 89 parts of $H_4P_2O_7$ are added with good agitation and mixing continued until all solids are completely dissolved. 209 parts of epichlorohydrin are charged while continuing to stir. The reaction mixture is then heated to 70°–80° C. and kept at this temperature for 2 hours. The reaction is complete when the theoretical reduction of the acid value has been obtained. Inorganic chloride (due to epichlorohydrin hydrolysis) is estimated by argentometric titration and found to be negligible.

The product is an aqueous solution of a compound having the following structure:

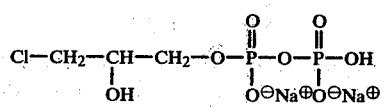

EXAMPLE II

Preparation of Reactant B 1000 parts of deionized water are charged into a reactor equipped with external heating and overhead stirring facilities. 446 parts of $Na_4P_2O_7 \cdot 10\ H_2O$ and 178 parts of $H_4P_2O_7$ are added with good agitation and mixing continued until complete dissolution is achieved. 320 parts of epichlorohydrin are charged while continuing to stir. The reaction mixture is then heated to 60°–80° C. and kept at this temperature for 3–4 hours. The reaction is monitored via acid/base titration and is deemed complete when the acid value has been reduced to a value approaching that of the theoretical one for a di-ester formation. The product formed is an aqueous solution of a compound having the following structure:

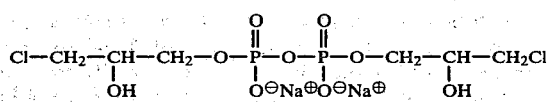

EXAMPLE III

Preparation of Reactant C 14.2 parts of phosphorous pentoxide are dispersed in 100 parts of methylene chloride using a suitable reactor equipped to exclude air moisture. With good agitation 16.1 parts of ethylene chlorohydrin are added and the reaction mixture kept at 35° C. for 2 hours. After removal of the solvent and subsequent purification the product obtained has the following structure:

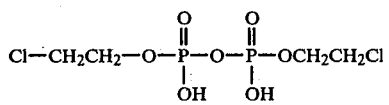

EXAMPLE IV

Preparation of Reactant D 14.2 parts of phosphorous pentoxide are dispersed in 100 parts of methylene chloride using a reactor capable of maintaining anhydrous conditions. 18.9 parts of 3-chloropropanol are added and the reaction mixture kept at 35°–37° C. for 3 hours. After removal of the solvent and purification the product obtained has the following structure:

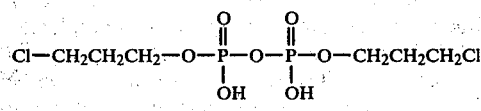

EXAMPLE V 62.9 parts of reactant "A" and 250 parts of deionized water are charged into a reactor equipped with external heating and overhead stirring facilities. The pH of the reaction mixture is adjusted to 8 with sodium hydroxide and 42.6 parts of lauryl dimethylamine are added. The mixture is stirred and heated at 80°–90° C. The progress of the reaction is monitored via argentometric estimation of chloride ion and the reaction is considered completed when all bound chlorine has been converted to chloride ion. The product obtained is a novel surfactant of the following structure:

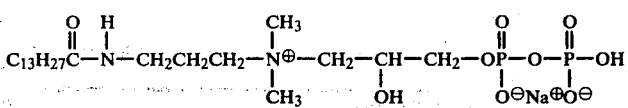

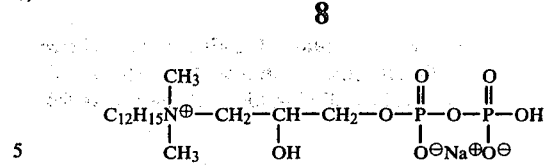

EXAMPLE VI 121.2 parts of reactant "C" and 600 parts of deionized water are mixed in a glass-lined reactor equipped with external heating and an overhead stirring apparatus. The pH of reaction mixture is adjusted to 8 with a 50% sodium hydroxide solution while stirring rapidly. 85.2 parts of laurly dimethylamine are added and the mixture is heated and stirred at 85°–90° C. for 8 hours. The progress of the reaction is followed via estimation of chloride ion produced. The reaction is deemed complete when all bound chlorine has been converted to chloride ion. The product obtained is an aqueous solution of a novel surfactant of the following structure:

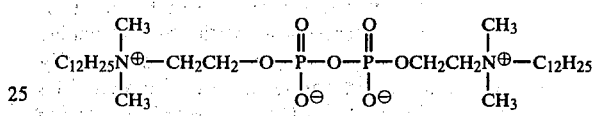

EXAMPLE VII 498 parts of reactant "A" and 1750 parts of deionized water are mixed in a glass-lined reactor equipped with an overhead stirrer and an external heating unit. The pH is raised by adding 25 parts of NaOH and under constant stirring the temperature is raised to 70° C. 426 parts of lauramidopropyl dimethylamine are added slowly. After the addition is completed the reaction mixture is stirred at 80° C. and the progress of the reaction is monitored via argentometric chloride titration. The reaction is complete after 4–5 hours and gives rise to a novel surfactant of the following structure:

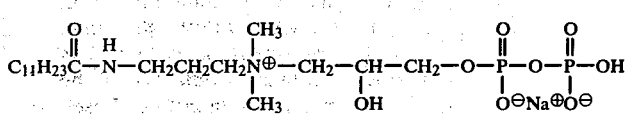

EXAMPLE VIII 250 parts of reactant "A" and 900 parts of deionized water are mixed in a suitable reactor having external heating and overhead stirring attachments. The pH is adjusted to 8 by adding 13 parts of NaOH with vigorous stirring and the temperature is raised to 70° C. 228 parts of myristamidopropyl dimethylamine are added slowly over a period of 30 minutes. After the addition is completed, the reaction mixture is stirred at 70°–80° C. and the progress of the reaction is monitored via argentiometric chloride titration. The reaction is complete after 5–6 hours yielding a novel surfactant of the following structure:

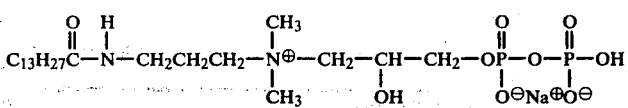

EXAMPLE IX 125 parts of reactant "B" and 700 parts of deionized water are mixed in a reactor described above. The pH is adjusted to between 7.5 and 8 by adding 6 parts of NaOH with vigorous stirring. After raising the temperature of the reaction mixture to 80° C. 214 parts of bis(2-hydroxyethyl) oleylamine are added and the reactant mixture stirred for 8 hours. The reaction product is a novel surfactant of the following structure:

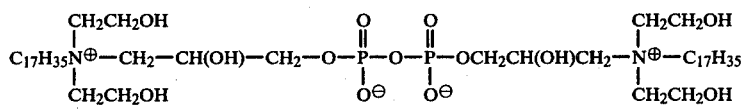

EXAMPLE X 200 parts of reactant "D" and 900 parts of deionized water are charged into a reactor equipped with heating and stirring facilities. The pH of the reaction mixture is adjusted to 8 with sodium hydroxide and 315 parts of octadecyl dimethylamine added to the reactor. The temperature is raised to 80° C. and the mixture stirred for 8 hours while monitoring the progress of the reaction via argentometric estimation of the conversion of bond chlorine to chloride ion. After 6 hours the reaction approaches completion. After isolation and purification a novel surfactant of the following structure is obtained.

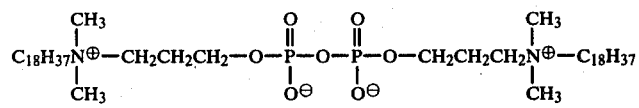

While the present invention has been described and illustrated with reference to certain preferred embodiments thereof, those skilled in the art will appreciate that various modifications, changes, omissions and substitutions can be made without departing from the spirit of the invention. It is intended, therefore that the invention be limited only by the scope of the appended claims.

What is claimed is:

1. A compound of the formula

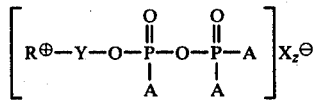

wherein A is selected from $-O^-$, $-OM$ and $-O-Y-R^+$ with the proviso that at least one A is $-O^-$;

$X^-$ is an anion;

z is an integer from 0 to 3;

R is an amidoamine moiety of the formula

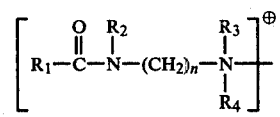

$R^1$ is selected from alkyl, alkenyl, alkoxy, or hydroxyalkyl of from 5 to 22 carbon atoms each, aryl or alkaryl of up to 20 carbon atoms;

$R^2$ is selected from hydrogen, alkyl, hydroxyalkyl or alkenyl of up to 6 carbon atoms each or cycloalkyl of up to 6 carbon atoms, or polyoxyalkylene of up to 10 carbon atoms;

$R^3$ and $R^4$ are the same or different and are selected from alkyl, hydroxyalkyl or carboxyalkyl of up to 6 carbon atoms and polyoxyalkylene of up to 10 carbon atoms; in addition, $R^3$ and $R^4$ taken together with the nitrogen to which they are attached, may represent an N-heterocycle, in which the Y radical is bonded to a ring atom of said N-heterocycle other than the nitrogen of the R moiety;

n is an integer from 2 to 12;

Y is selected from alkylene, optionally interrupted by up to 3 oxygen atoms, of up to 12 carbon atoms, or substituted alkylene substituted with alkyl, alkoxy, hydroxy or hydroxyalkyl, of not more than 10 carbon atoms each;

M is selected from hydrogen, an organic radical selected from alkyl or hydroxyalkyl of up to 6 carbon atoms, polyhydroxyalkyl of up to 10 carbon atoms, glyceryl, cycloalkyl of up to 6 carbon atoms, aryl or arylalkyl of up to 10 carbon atoms, or a salt radical selected from alkali metals and alkaline earth metals.

2. The compound of claim 1 wherein $R_3$ and $R_4$ are methyl.

3. The compound of claim 1 of the formula

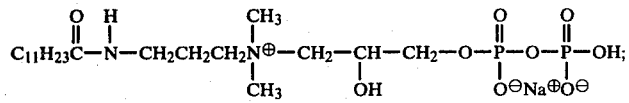

4. The compound of claim 1 of the formula

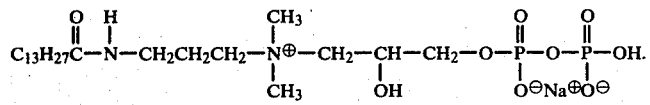

* * * * *